United States Patent [19]

Mombrinie

[11] Patent Number: 5,197,975
[45] Date of Patent: Mar. 30, 1993

[54] RADIOLUCENT SPINE SUPPORT FRAME

[76] Inventor: Bruno Mombrinie, 5110 Gravenstein Hwy. North, Sebastopol, Calif. 95472

[21] Appl. No.: 727,575

[22] Filed: Jul. 9, 1991

Related U.S. Application Data

[63] Continuation-in-part of Ser. No. 295,253, Jan. 9, 1989, Pat. No. Des. 322,312, and a continuation-in-part of Ser. No. 488,966, Mar. 6, 1990.

[51] Int. Cl.⁵ .......................... A47C 27/08; A61H 7/00
[52] U.S. Cl. .................................... 606/238; 606/240; 5/601; 5/909; 128/845; 378/209
[58] Field of Search ....................... 128/54, 60, 61, 845, 128/69, 70; 606/201, 237, 238, 240; 378/208, 209; 5/600, 601, DIG. 909; 108/55.3

[56] References Cited

U.S. PATENT DOCUMENTS

| | | | |
|---|---|---|---|
| 2,633,844 | 4/1953 | Herndon | 128/60 X |
| 3,298,363 | 1/1967 | Parkin . | |
| 3,645,257 | 2/1972 | Nakayama | 128/60 |
| 3,656,190 | 4/1972 | Regan et al. . | |
| 3,999,234 | 12/1976 | Regan . | |
| 4,421,110 | 12/1983 | DeLisle et al. | 128/60 |
| 4,707,872 | 11/1987 | Hessel | 5/451 |
| 5,056,507 | 10/1991 | Yum | 128/61 |
| 5,080,090 | 1/1992 | Liau et al. | 128/60 |

FOREIGN PATENT DOCUMENTS 18840 of 1913 United Kingdom .................. 128/60

Primary Examiner—Randall L. Green
Assistant Examiner—Mary Beth O. Jones

[57] ABSTRACT

A radiolucent spine support frame has independently adjustable supports and other features making the frame easy to use, maintain and transport and embraces a support having a radiolucent base on which are mounted four independently adjustable supports having gel cushions on top of each support to contact the patient's body and support the patient during surgical or medical procedures, especially back surgery or x-ray examination of the spine.

14 Claims, 7 Drawing Sheets

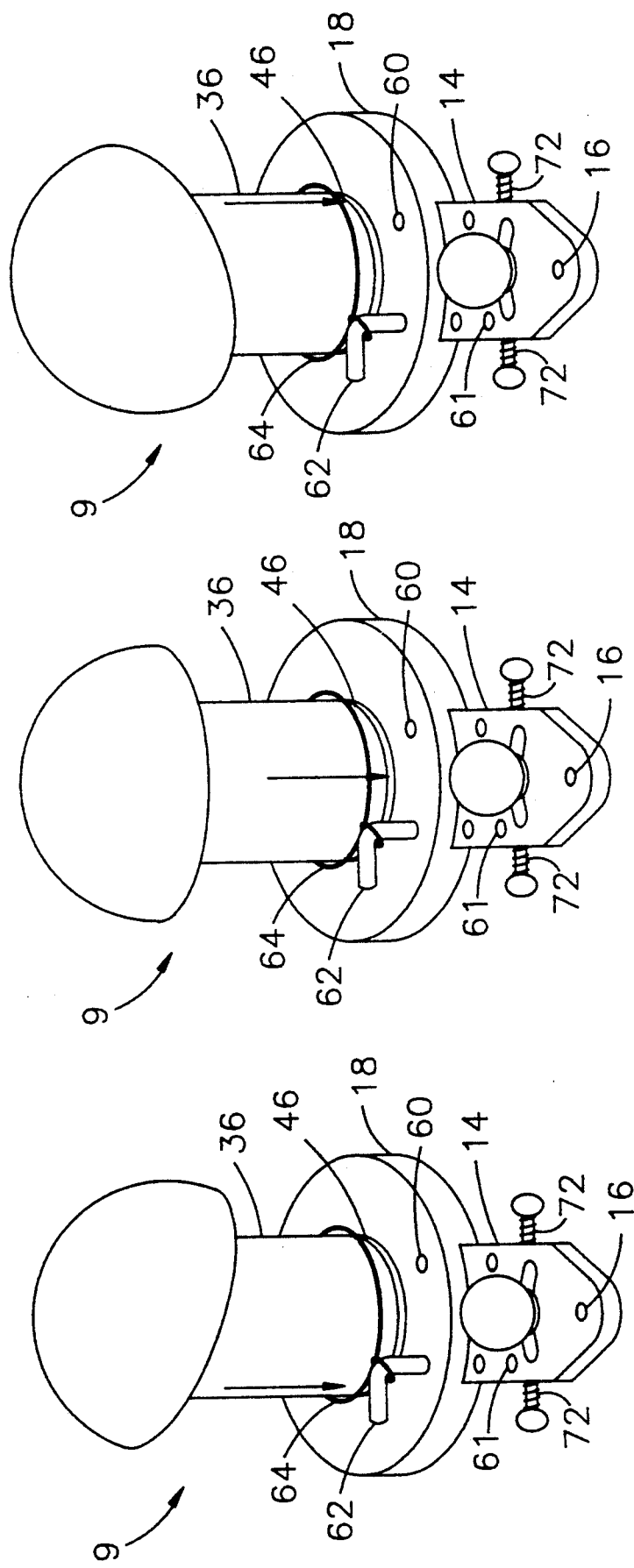

RADIOLUCENT SPINE SUPPORT FRAME

This application is a continuation-in-part of pending U.S. patent application Ser. No. 07/295,253 (filed Jan. 9, 1989), now design U.S. Pat. No. 322,312 and 07/488,966 (filed Mar. 6, 1990).

BACKGROUND OF THE INVENTION

The invention relates to the field of support frames for use in medical procedures. More particularly, the invention relates to frames for supporting the body of a patient, particularly for supporting the spine. Even more specifically, the invention relates to a support frame for use in medical and surgical procedures directly involving the spine of the patient.

In the past, spine support frames have been used in medical procedures and operations involving the spine. In those spine support frames, the pads used to support the patient moved in unison. The inability to adjust the pads independently of one another made use and adaptation of the spine frame difficult, especially when dealing with patients having severe spinal deformities such as scoliosis.

SUMMARY OF THE INVENTION

The present invention encompasses a radiolucent spine support frame having independently adjustable supports and other features making the frame easy to use, maintain and transport.

More specifically, the invention embraces a support frame having a radiolucent base on which are mounted four independently adjustable supports. Gel cushions are located on top of each support to contact the patient's body and support the patient during surgical or medical procedures, such as back surgery or x-ray examination of the spine. Additionally, the support frame of the invention contains means for fixing the position of the various gel cushion supports once the proper positioning has been determined for the particular patient and procedure.

The radiolucent base is preferably a combination of two rectangular radiolucent sheets joined by walls along the edges of the sheets. Preferably, a space between the sheets serves as a slot for inserting an x-ray cassette.

The spine support frame preferably has four support columns. Each column is mounted on a slide plate, which in turn is mounted on a pivot bar. Thus, the support frame of the invention has four pivot bars, each pivotable about its own pivot point on the surface of the upper or first rectangular sheet. Each slide plate includes a groove on the side facing the first rectangular sheet. The groove engages the pivot bar and allows the slide plate and attached column to be moved controllably along the pivot bar. The slide plate groove diametrically traverses the slide plate. Preferably, the groove has a dove-tail shape which corresponds to a dove-tail shaped pivot bar. The relative position of a support column on the surface of the first sheet can be adjusted, either by moving the slide plate relative to the pivot bar, by moving the pivot bar about the pivot point or by employing both types of movement.

The relative positions of the support columns can be fixed by locking means in the support tray. Both the position of the pivot bar with respect to the first plate and the position of the sliding plate on the pivot bar can be fixed.

Each pivot bar preferably has two different means for fixing the position thereof. In the first means, an arcuate slot passes through the pivot bar. This arcuate slot is positioned near each pivot point on the pivot bar and is positioned directly above a threaded hole in the first plate. A washer rests on top of each arcuate slot. Knobs, each having a threaded protrusion, are positioned with their threaded protrusions extending through respective washers and arcuate slots to engage the respective threaded holes located in the first sheet. In this way, when the desired position of a pivot arm is achieved, the knob for that pivot arm can be tightened to secure the pivot arm in position. This procedure can be followed to secure each pivot arm by tightening its respective knob.

The position of the pivot arm is further maintained by a pair of threaded set screws mounted in threaded passageways in each of said pivot bars. Each threaded passageway enters the pivot bar on each of the sides of the pivot bar not facing or opposing the first plate. Each threaded passageway is straight and enters the side at a right angle. The threaded passageways enter the side at a point generally at the middle of the height of the arc of the arcuate slot.

The threaded set screws are mounted into the threaded passageways until the end of each threaded set screws interior of the pivot bar makes contact with the portion of the threaded protrusion of the knobs passing through the arcuate slot, thereby preventing further pivoting motion of the pivot bar about the pivot point.

The position of the slide plate on the pivot bar is also lockable through means in the support tray. Each pivot bar has a plurality of mounting holes placed on the face of the pivot bar opposite said first plate. Each slide bar has two circular perforations therethrough. These circular perforations are equally distant from and on the same side of the support column on the side plate. These circular perforations pass from the face of the slide plate, wherein the cylindrical support is mounted, through to the diametrically traversing slot on the opposite side of the slide plate.

The circular perforations in the slide plate line up with the center of the mounting holes on the pivot bar. The mounting holes, although positioned in pairs along the pivot bar, are placed so that the imaginary line connecting each pair of holes does not intersect the axis of the pivot bar at a right angle. This placement of the mounting holes allows a greater range of adjustable positions for the slide plate with respect to the pivot bar.

The slide plate position is maintained by insertion of a pin through the cylindrical perforations into the mounting holes on the pivot bar. The pin is preferably connected to the slide plate by the use of string or fishing line or other suitable means to prevent the pin from being lost or stored away from the support tray. The end of the pin inserted into the mounting holes is tapered for ease of insertion. The circular perforations on the slide plate are of a larger diameter than the mounting holes on the pivot bar, further allowing ease of insertion of the pin. The pin is generally angled to further facilitate insertion. Once the pin is inserted through a hole in the slide plate into the mounting hole on the pivot bar, the position of the slide plate with respect to the pivot bar is maintained.

Each pivot bar preferably has an end boss protruding upwardly from the pivot bar at the distal end of the pivot bar. The end boss prevents the slide plate from moving off the pivot bar at the distal end.

The support columns, each mounted on a different slide plate, are preferably cylindrically shaped. About the base of each column, rests an annular washer or O-ring. Additionally, a sleeve is mounted on each column. The sleeves are preferably cylindrically shaped. The top end of each sleeve is angled obliquely with respect to the length of the sleeve and its respective column. An end plate is attached to the oblique angled end of each sleeve. A gel cushion is attached to each end plate. The position of the gel cushion can be rotated relative to its respective column by a rotation of its respective sleeve. Also, the relative height of each particular gel cushion can be varied by replacing a sleeve of one height with a sleeve of a different height.

Additional features of the spine support frame of the invention include the presence of perforations in the first sheet near opposite edges. These perforations serve as handles for carrying the frame. The frame may also be equipped with anti-skid runners on the bottom of the second sheet which prevent the base of the frame from moving during use.

These and other features of the invention are further shown in the drawings and detailed description.

BRIEF DESCRIPTION OF THE DRAWINGS

FIGS. 4a–4c show a column and pivot arm from the spine support frame shown in FIG. 1.

DETAILED DESCRIPTION OF THE INVENTION

The invention will now be described with respect to the preferred embodiment illustrated in FIGS. 1 through 6.

Figure 1:
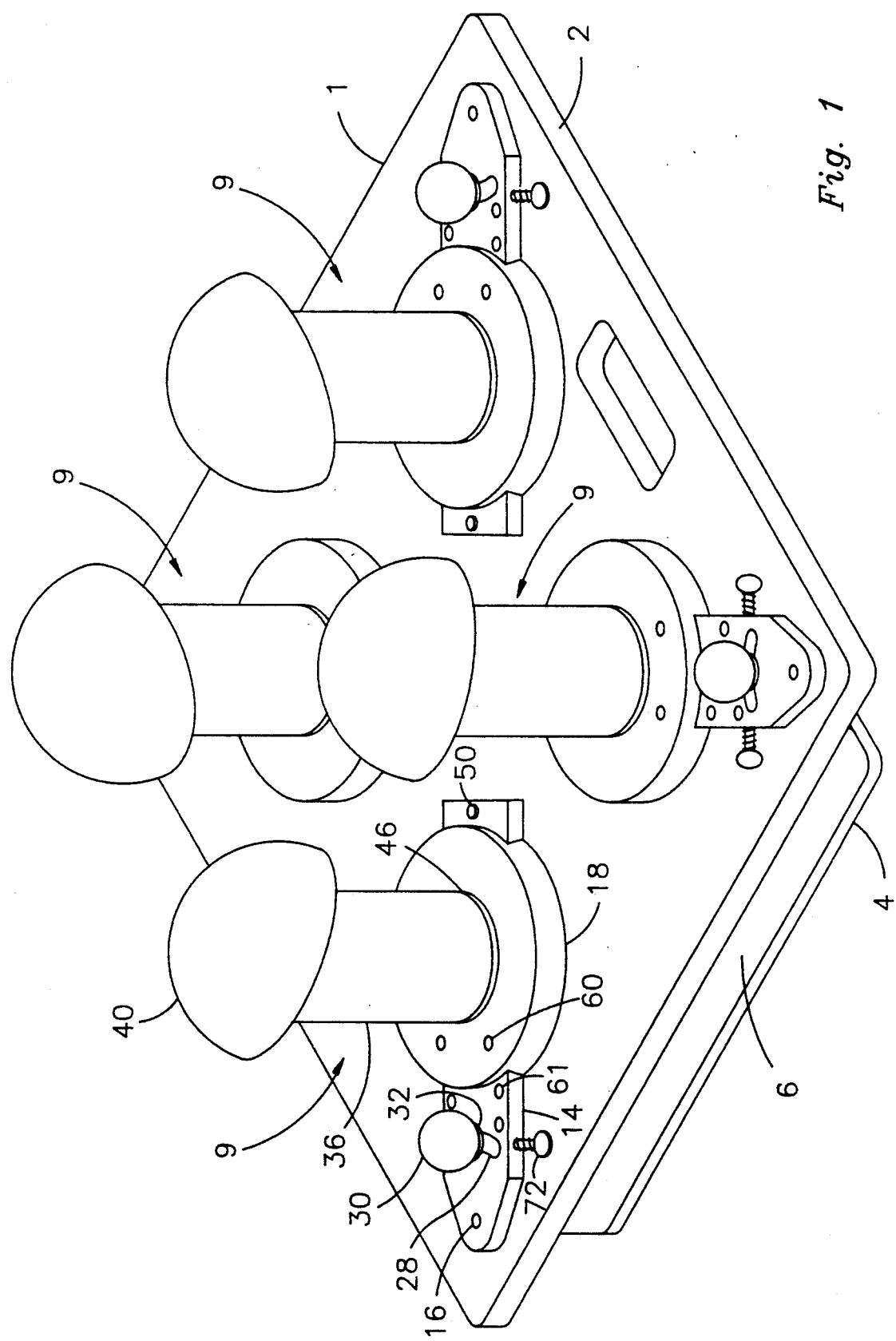
FIG. 1 shows a perspective view of a preferred embodiment of the invention.
Figure 2:
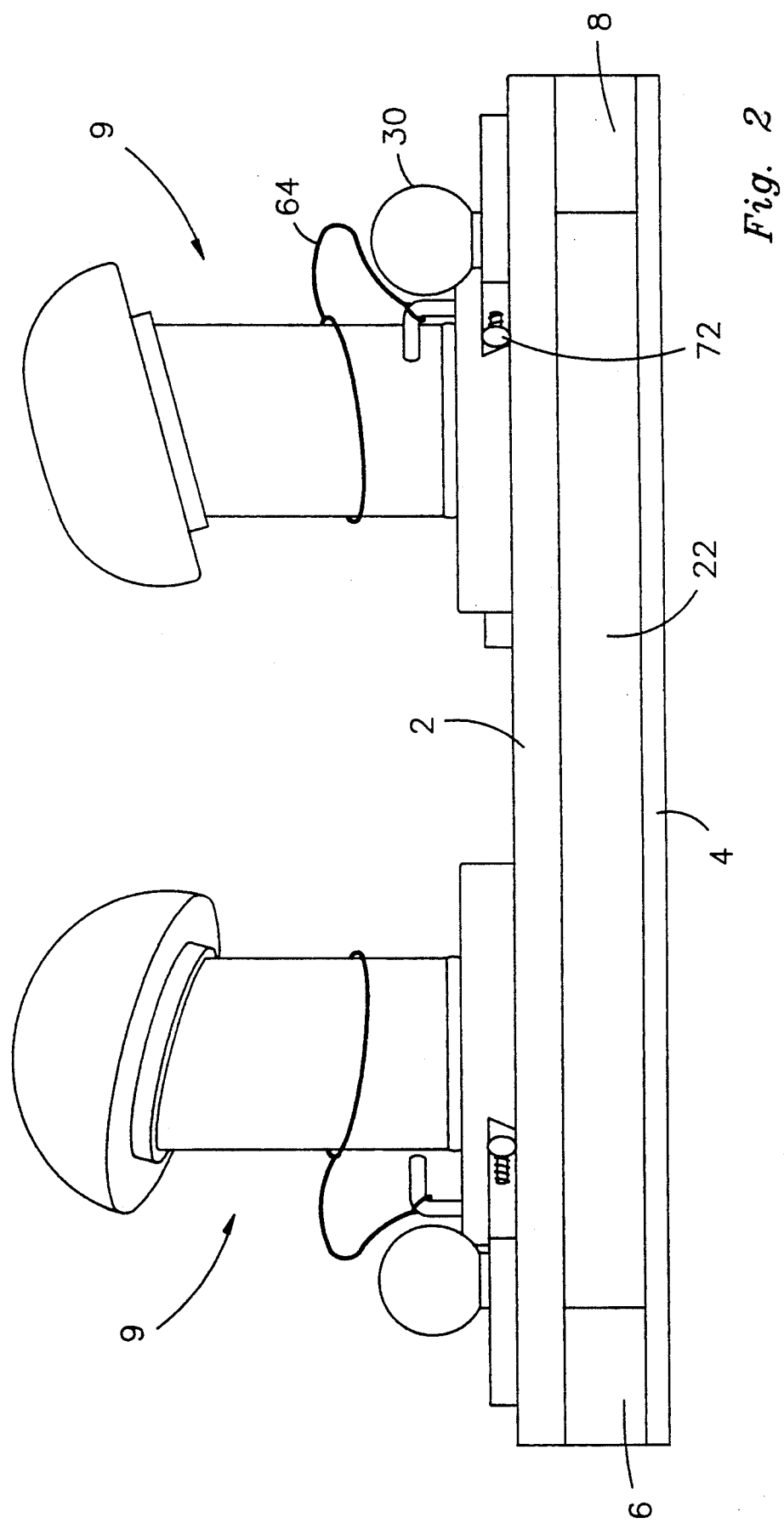
FIG. 2 shows a side view of the spine frame of FIG. 1 looking through the cassette slot.

FIG. 1 shows the radiolucent spine support frame 1 having a first rectangular sheet 2 and a second rectangular sheet 4 which, together with walls 6 and 8 (wall 8 is shown in FIG. 2), form the base of frame 1. Sheets 2 and 4 and walls 6 and 8 are joined together along the sheet edges leaving a slot 22.

Figure 6:
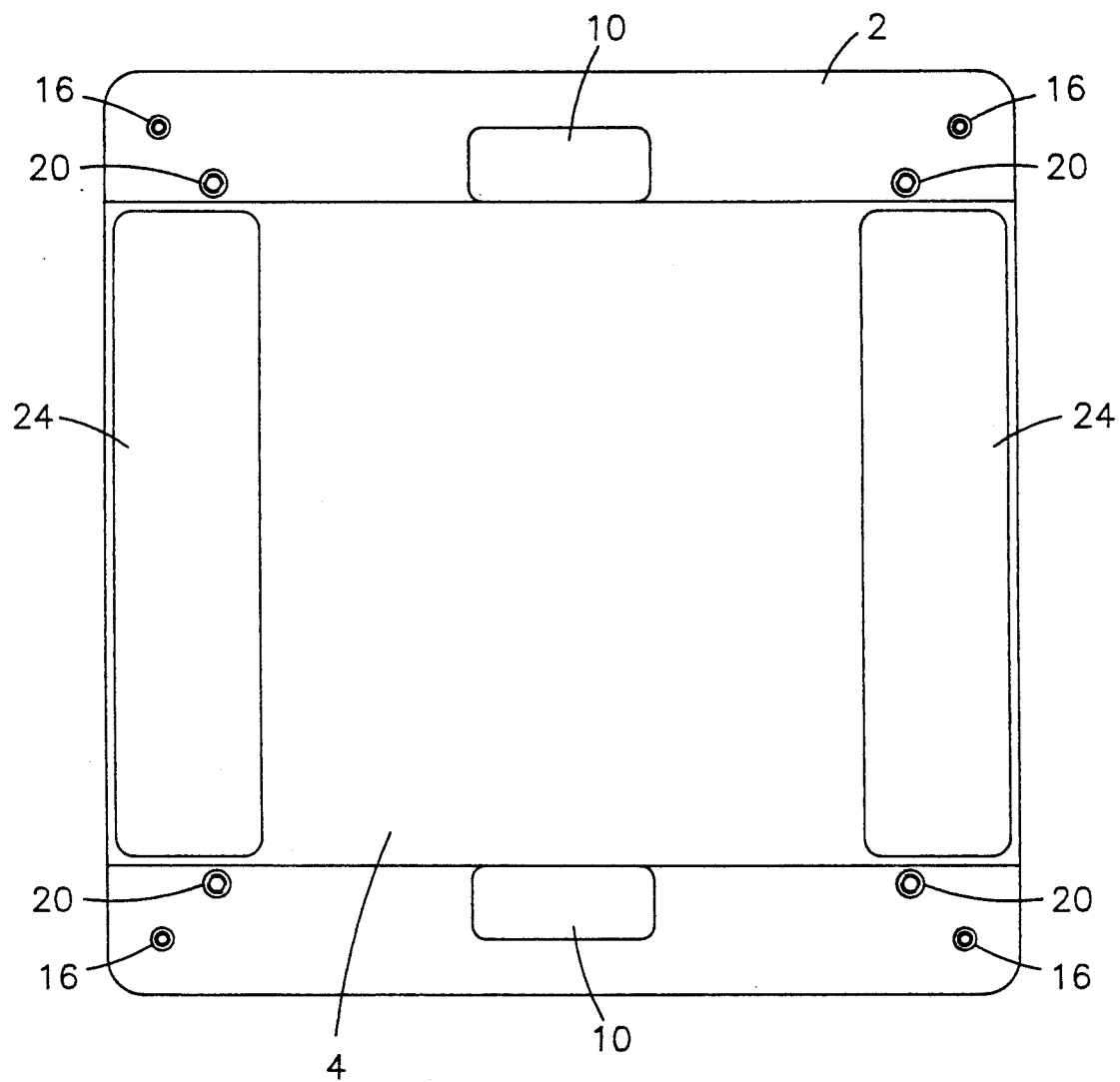
FIG. 6 is a bottom view of the spine support frame of FIG. 1.
Figure 7:
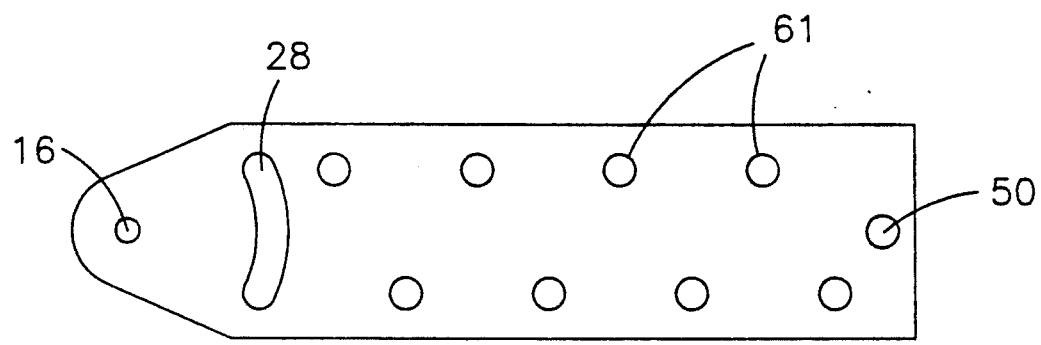
FIG. 7 shows a top view of a pivot bar with the slide plate, knob, washer and set screws all removed.
Figure 8:
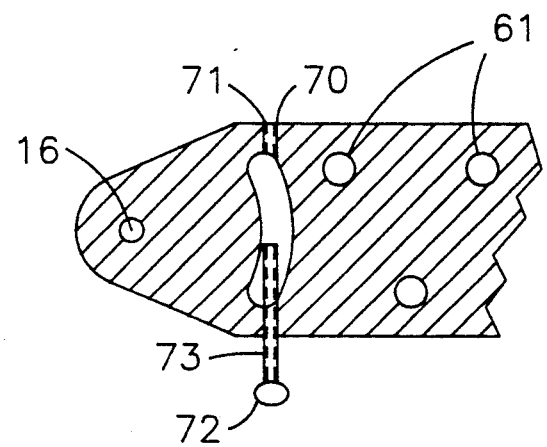
FIG. 8 shows a sectional view of FIG. 7 of the slide plate, illustrating the threaded passageways.
Figure 9:
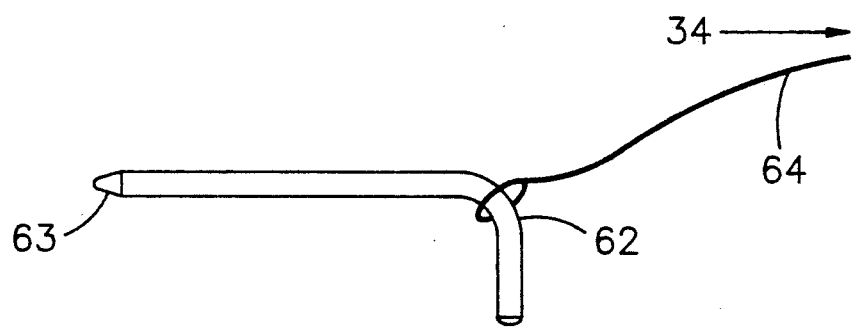
FIG. 9 shows the pin.

The second sheet 4 preferably has two anti-skid runners 24 mounted on the bottom of sheet 4 at opposite edges of sheet 4 as shown in FIG. 6. First sheet 2 preferably has two perforations 10 near opposite edges of first sheet 2 which serve as handles for carrying frame 1. Second sheet 4 is preferably equal in width to first sheet 2, however, second sheet 4 is preferably shorter in length than first sheet 2. In this way, second sheet 4 is not co-extensive with first sheet 2 in the areas of first sheet 2 corresponding to the positions of perforations 10. The invention also encompasses devices which do not have perforations for handles or in which the relative sizes of the two sheets differ from those shown in the preferred embodiment.

Figure 3:
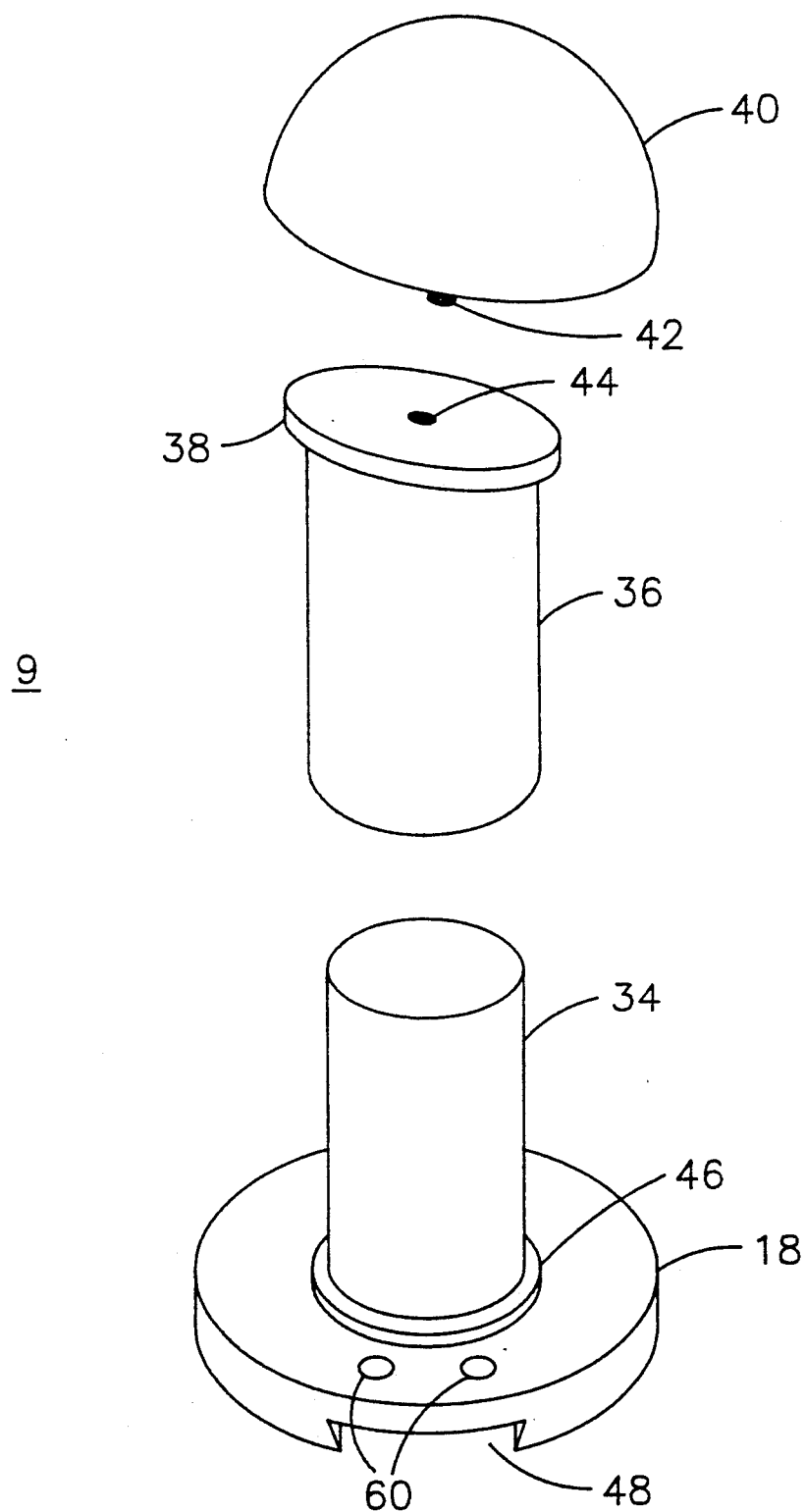
FIG. 3 is an exploded view of a support column from the gel cushion down through the column end and slide plate.

The frame 1 additionally contains four supports 9 which rise vertically above the surface of first sheet 2. An exploded view of a support 9 is shown in FIG. 3.

Each support 9 comprises a column 34 fixed to a slide plate 18. An O-ring 46 is positioned around the base of each column 34. Each support 9 further comprises a sleeve 36 which fits over column 34 and rests on O-ring 46. An end plate 38 is attached at the top of each sleeve 36. Preferably, each end plate 38 is at an oblique angle with respect to the length of its respective sleeve 36.

A gel cushion 40 is attached to each end plate 38. This attachment can be by any known means. The gel in cushions 40 is preferably a thixotropic polymer gel which conforms to the shape of the patient. The gel is preferably coated with a vinyl-based paint. Preferably, each gel cushion 40 has a threaded protrusion 42 adapted to engage a respective threaded hole 44 in its respective end plate 38. Each sleeve 36 is designed to fit over its respective column 34.

The slide plates 18 are positioned on pivot bars 14 located on first sheet 2. Each pivot bar 14 is rotatable about a respective pivot point 16. The pivot bars 14 are secured to first sheet 2 at their respective pivot points. The four pivot points 16, in the preferred embodiment, are each located near a corner of first sheet 2. Each slide plate 18 has a groove 48 (as shown in FIG. 3) which diametrically traverses the side of the slide plate 18 facing first sheet 2. Each slide plate 18 fits over its respective pivot bar 14 along groove 48. Preferably, each slide plate groove 48 is dove-tail shaped and corresponds to its respective dove-tail shaped pivot bar 14. The dove-tail configuration prevents the slide plate 18 from disengaging its respective pivot bar 14. Each pivot bar 14 has an end boss 50 located at its distal end to prevent its respective slide plate 18 from sliding off pivot bar 14.

Slide plates 18 have circular perforations 60 passing therethrough. Circular perforations 60 are equally distant from the axis of cylindrical column 34 and pass through slide plate 18 from the face opposite first sheet 2 communicating with slide plate grove 48.

Pivot bars 14 are equipped with a plurality of mounting holes 61 on the face opposite first sheet 2. Mounting holes 61 are placed in pairs generally along the axial direction of pivot bars 14. Although placed in pairs, mounting holes 61 are positioned so that an imaginary line joining a pair of mounting holes 61 is not perpendicular to the longitudinal axis of the pivot bar 14.

Circular perforations 60 are of greater diameter than mounting holes 61. The end 63 of pin 62 is tapered to facilitate placement of pin 62 through circular perforations 60 and into mounting holes 61 while frame 1 is in use. To prevent pin 62 from being lost, retainer 64 attaches pin 62 to cylindrical column 34. Said retainer 64 is preferably fishing line tying pin 62 to column 34.

In the preferred embodiment, each pivot bar 14 has an arcuate slot 28 running through pivot bar 14 near its respective pivot point 16. The arc of each slot 28 corresponds to the direction of rotation of its respective pivot bar 14 about its respective pivot point 16. A threaded hole 20 is located in first sheet 2 immediately beneath each slot 28. A washer 32 is placed immediately over each slot 28. Knobs 30, each having a threaded protrusion 52, are placed so that respective threaded protrusions pass through respective washers 32 and slots 28 and engage respective threaded holes 20.

The preferred embodiment allows the position of pivot bar 14 to be further secured in position. Each pivot bar 14 has two straight threaded passageways 70 mounted therein. Threaded passageways 70 begin on the side of pivot bar 14 not facing or opposing first sheet 2. Straight passageways 70 enter the side of pivot bar 14 at a point on the side of the pivot bar 14 mid-way to the height of the arc of arcuate slot 28. Threaded passageways 70 pass through to arcuate slot 28. A set screw 72 has threads 73 matching threads 71 in passageways 70. The base, pivot bars, slide plates, columns and sleeves are preferably made of a radiolucent acrylic plastic.

Figure 5A:
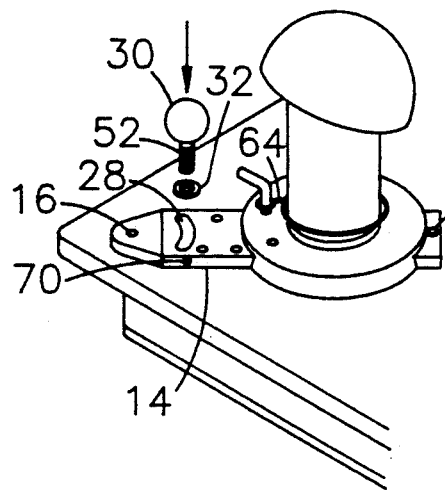
FIGS. 5a–5d show a corner of the spine support frame shown FIG. 1 including movement of the pivot arm and support column.
Figure 5B:
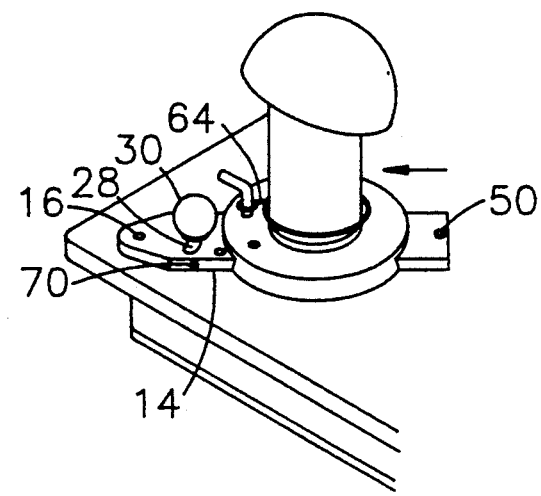
Figure 5C:
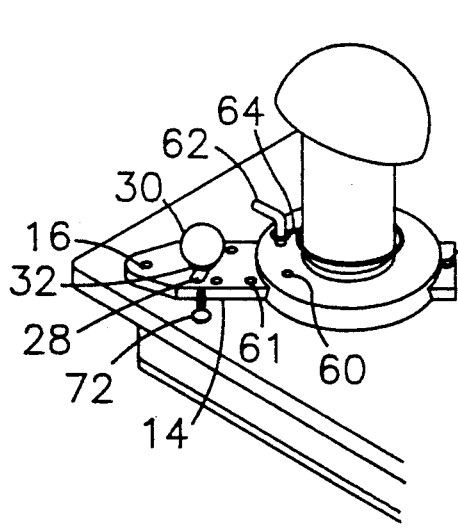
Figure 5D:
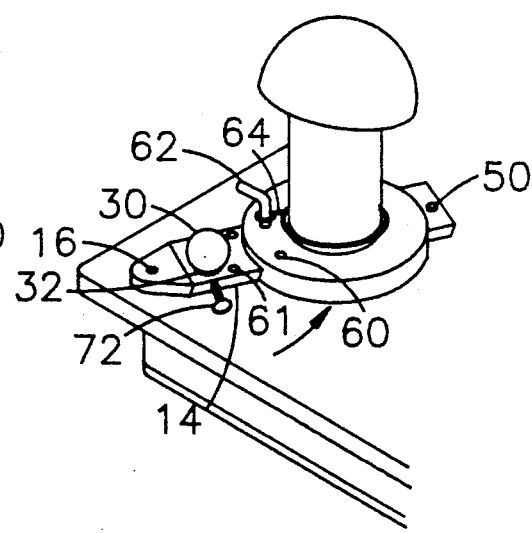

To use the spine support frame of the invention, the patient is placed prone with the patient's abdomen hanging freely down between supports 9. In this way, the gel cushions 40 can be attached to end plates 38 by merely screwing the gel cushions 40 into the end plates 38. Each sleeve 36, and hence gel cushion 40, can be rotated relative to its respective column 34 and slide plate 18, as shown in FIGS. 4a–4c. Also, the relative height of each sleeve 36 can be varied by substituting sleeves of differing heights. Each slide plate 18 can be moved along its respective pivot bar 14, as shown in FIG. 5a and 5b. Placement of mounting holes 61 in a staggered pair configuration allows slide plate 18 to be locked into a greater number of positions with respect to pivot bar 14. When slide plate 18 is positioned on pivot bar 14, one of circular perforations 60 of slide plate 18 aligns with one of mounting holes 61. Pin 62 is placed through circular perforations 60 and into mounting holes 61, thereby generally locking the position of slide plate 18 with respect to pivot bar 14. In addition to movement along its respective pivot bar 14 and rotation of its respective sleeve 36 about column 34, the position of each gel cushion 40 can be varied by rotation of its respective pivot bar 14 about pivot point 16 along the surface of first sheet 2. This pivoting movement is illustrated in FIGS. 5c and 5d. Once pivot bar 14 has been rotated to a desired position, it may be fixed in place using fixing means. To fix the position of each pivot bar 14, one tightens its respective knob 30. It should be understood that, while the preferred embodiment has been described using a knob-type fixing means, any known fixing means could also be employed. Further, the knobs could be in the shape of any other known gripping or turning device. Set screw 72 is inserted into the passageway 70 and adjusted so that end point 74 of set screw 72 contacts knob protrusion 52 above first sheet 2. With set screw 72 locked in place by threads 73 of set screw 72 and threads 71 of passageway 70, pivotal motion of pivot arm 14 is impeded. Once a desired position of the patient is achieved, supports 9 are then locked into place using knobs 30 set screws 72 and pins 62. After the desired procedure (such as surgery or x-ray examination) has been performed, gel cushions 40 may be removed from frame 1 and either replaced or cleaned with disinfectant. Gel cushions 40 used in preferred embodiment are circular and oversized, however, any suitable cushion shape may be employed without departing from the scope of the invention.

While the invention has been described with respect to the preferred embodiment, it is understood that other variations may be made in the particular components or configuration of the spine support frame of the invention without departing from the scope of the invention.

What is claimed is:

1. A frame for supporting a patient during medical proceedings comprising:
 a. a radiolucent base;
 b. a plurality of adjustable height columnar means for supporting said patient above and spaced from said base;
 c. means for adjustably positioning said columnar means along the surface of said base;
 d. means for releasably fixing said columnar means to said base within a continuum of positions.

2. The frame of claim 1 further comprising means, connected to said columnar means remote from said base, for cushioning said patient being supported.

3. The frame of claim 1 wherein said base comprises a) a pair of spaced apart rectangular rigid sheets; b) a plurality of pivot bars attached to respective mounting means, the mounting means being mounted to an upper one of said sheets at each of the four corners of said upper sheet c) means for adjustably positioning said pivot bars angularly about said mounting means on said upper one of said sheets, d) said pivot bars having an end boss distal the mounting means on the face opposite the base, said plurality of columnar means being supported by respective pivot bars.

4. The frame of claim 3 wherein said base further comprises:
 a. perforations in said sheets forming handles for transporting said frame;
 b. two anti-skid runners mounted on the bottom one of said sheets.

5. The frame of claim 3 wherein said columnar means comprises:
 a. a support column having upper and lower ends;
 b. a sliding plate perpendicularly attached to the lower end of said support column, having a groove diametrically traversing the lower surface for engagement with each of said pivot bars;
 c. an annular ring circumscribing each support column and resting on said sliding plate;
 d. a sleeve member fitting over said support column, resting movably on said annular ring, said upper end of said sleeve member having an obliquely angled surface, with a threaded hole in its center;
 e. a gel cushion having an extending threaded portion mounted into each of said threaded holes.

6. The frame of claim 5 wherein said means for releasably fixing said columnar means to said base at a selected one of said adjustable positions comprises:
 a. an arcuate slot through each of said pivot bars near said mounting means, above a respective threaded fastening hole in the upper one of said sheets;
 b. a washer resting on each of said pivot bars, above said respective threaded fastening holes;
 c. a knob with a threaded downwardly extending portion passing through each said washer and each said arcuate slot, into said respective threaded fastening hole.

7. The frame of claim 6 said fixing means further comprising:
 a. straight threaded passageways entering said pivot bars on the side of the pivot bar not facing or opposing the upper one of said sheets, communicating with a point midway the height of said arcuate slot;
 b. a threaded pin in each of said straight, threaded passageways with the end contacting said threaded downwardly extending portion of said knobs.

8. The frame of claim 7 wherein said means for releasably fixing said columnar means to said base at a selected one of said adjustable positions further comprises:

a. two holes in each of said sliding plates passing through the upper surface thereof, each of said holes communicating with said diametrically traversing groove;
b. a plurality of mounting holes placed in a pair of linear arrays on each of said pivot bars, said holes being positioned to align with at least one of said holes in said sliding plates, said mounting holes having a diameter generally smaller than the diameter of said holes in said sliding plates;
c. a pin being placed into at least one of said holes in said sliding plates through to said mounting holes, said pin being tapered at the end of insertion, said pin being angled at the end opposite the end of insertion;
d. means for connecting each of said pins to a different one of each of said support columns.

9. The frame of claim 6 wherein said means for releasably fixing said columnar means to said base at a selected one of said adjustable positions further comprises:
a. two holes in each of said sliding plates passing through the upper surface thereof, each of said holes communicating with said diametrically traversing groove;
b. a plurality of mounting holes placed in a pair of linear arrays on each of said pivot bars, said holes being positioned to align with at least one of said holes in said sliding plates, said mounting holes having a diameter generally smaller than the diameter of said holes in said sliding plates;
c. a pin being placed into at least one of said holes in said sliding plates through to said mounting holes, said pin being tapered at the end of insertion, said pin being angled at the end opposite the end of insertion;
d. means for connecting each of said pins to a different one of each of said support columns.

10. The frame of claim 5 wherein said means for releasably fixing said columnar means to said base at a selected one of said adjustable positions comprises:
a. holes in said sliding plates passing through the upper surface thereof, communicating with said diametrically traversing groove;
b. a plurality of mounting holes in linear arrays on each of said pivot bars, to align with at least one of said holes in said sliding plates, said mounting holes having a diameter generally smaller than the diameter of said holes in said sliding plates;
c. a pin being placed into at least one of said holes in said sliding plates through to said mounting holes, said pin being tapered at the end of insertion, said pin being angled at the end opposite the end of insertion;
d. means for connecting each of said pins to a different one of each of said support columns.

11. The frame of claim 3 wherein said means for releasably fixing said columnar means to said base at a selected one of said adjustable positions comprises:
a. an arcuate slot through each of said pivot bars near said mounting means above a respective threaded fastening hole in the upper one of said sheets;
b. a washer resting on each of said pivot bars, above said respective threaded fastening hole;
c. a knob with a threaded downwardly extending portion passing through each said washer and each said arcuate slot, into said respective threaded fastening hole.

12. The frame of claim 11 said fixing means further comprising:
a. threaded passageways entering each of said pivot bars on sides of the pivot bars not facing the upper sheet communicating with a point midway the height of said arcuate slot;
b. a threaded pin in each of said passageways with the end of each of said threaded pins contacting said threaded downwardly extending portion of said knobs.

13. The frame of claim 1 wherein said columnar means comprises:
a. a support column having upper and lower ends;
b. a sliding plate integrally formed perpendicularly to the lower end of said support column;
c. an annular ring circumscribing each support column and resting on said sliding plate;
d. a sleeve member fitting over each of said support columns, resting movably on said annular ring, said sleeve having the end distal to said sliding plate having an obliquely angled surface, said obliquely angled surface having a threaded hole in its center;
e. a gel cushion having an extending threaded portion mounted into each of said threaded holes.

14. A frame for supporting a patient during medical proceedings comprising:
a. a radiolucent base, comprising:
  i. two rectangular sheets joined at the edges, one above the other, by two walls forming a slot therebetween;
  ii. two perforations in the upper one of said sheets forming handles for transporting said frame;
  iii. two anti-skid runners mounted on the bottom facing side of said sheets;
  iv. four pivot bars mounted to the upper one of said sheets at each of the four corners of upper one of the said sheets by means allowing said pivot bars to be adjustably positioned angularly about said mounting means on said upper one of said sheets;
  B. having an end boss distal the mounting means on the face opposite the base;
  C. having walls not facing or opposite said upper one of said sheets diverging in the direction away from said sheets
b. a plurality of columnar means for supporting said patient above and spaced from said base, each of said columnar means comprising:
  i. a cylindrical support column having a upper and bottom end;
  ii. a circular sliding plate integrally formed perpendicularly to the bottom of said cylindrical support column, said circular sliding plate having a dove-tail groove diametrically traversing the lower surface thereof for engagement with said diverging walls of said pivot bars;
  iii. an annular ring circumscribing each cylindrical support column and resting on said circular sliding plate;
  iv. a cylindrical sleeve member fitting over each of said cylindrical support columns, resting movably on said annular ring, having the end distal to said circular sliding plate obliquely angled, said obliquely angled surface having a threaded hole in its center;
  v. a gel cushion having an extending threaded portion mounted into each of said threaded holes
c. said columnar means being adjustably positionable on said base by moving said sliding plates along said pivot bars between said mounting means and an end boss projecting on each pivot bar on the end distal to the mounting means and pivoting said pivot bars about said mounting means d. means for releasably fixing said columnar means to said base at a selected one of said adjustable positions, comprising:
  i. an arcuate slot through each of said pivot bars near said mounting means, placed above a respective threaded fastening hole in the upper one of said sheets;
  ii. a washer resting on each of said pivot bar, above said threaded fastening hole;
  iii. a knob with a threaded downwardly extending portion passing through said washer and said arcuate slot, into said threaded fastening hole;
  iv. two straight, threaded passageways entering each of said pivot bars on the side of the pivot bar not facing or opposing the upper one of said sheets, communicating with a point midway the height of said arcuate slot;
  v. a threaded pin being placed into each of said straight, threaded passageways with the end of each of said threaded pins contacting said threaded downwardly extending portion of said knobs;
  vi. two holes in each of said sliding plates passing through the upper surface thereof, each of said holes communicating with said diametrically traversing groove;
  vii. a plurality of mounting holes placed in a pair of linear arrays on each of said pivot bars, said holes being positioned to align with at least one of said holes in said sliding plates, said mounting holes having a diameter generally smaller than the diameter of said holes in said sliding plates;
  viii. a pin being placed into at least one of said holes in said sliding plates through to said mounting holes, said pin being tapered at the end of insertion, said pin being angled at the end opposite the end of insertion;
  ix. means for connecting each of said pins to a different one of each of said support columns.

* * * * *